(12) United States Patent
Chen et al.

(10) Patent No.: US 7,991,116 B2
(45) Date of Patent: Aug. 2, 2011

(54) MONOCHROMATIC X-RAY MICRO BEAM FOR TRACE ELEMENT MAPPING

(75) Inventors: Zewu Chen, Schenectady, NY (US); Ning Gao, Niskayuna, NY (US); Walter Gibson, Voorheesville, NY (US)

(73) Assignee: X-Ray Optical Systems, Inc., East Greenbush, NY (US)

( * ) Notice: Subject to any disclaimer, the term of this patent is extended or adjusted under 35 U.S.C. 154(b) by 0 days.

(21) Appl. No.: 12/063,334

(22) PCT Filed: Jul. 26, 2006

(86) PCT No.: PCT/US2006/028890
§ 371 (c)(1),
(2), (4) Date: Feb. 8, 2008

(87) PCT Pub. No.: WO2007/019053
PCT Pub. Date: Feb. 15, 2007

(65) Prior Publication Data
US 2009/0161829 A1    Jun. 25, 2009

Related U.S. Application Data

(60) Provisional application No. 60/705,376, filed on Aug. 4, 2005.

(51) Int. Cl.
*G21K 1/06* (2006.01)
*G21K 1/00* (2006.01)
(52) U.S. Cl. .................. 378/84; 378/85; 250/503.1
(58) Field of Classification Search .............. 378/84, 378/85, 145, 156, 159; 250/503.1; 356/331–334; 385/8–10, 68, 129–132
See application file for complete search history.

(56) References Cited

U.S. PATENT DOCUMENTS
2,688,094 A * 8/1954 Dumond .................. 378/85
(Continued)

FOREIGN PATENT DOCUMENTS
GB    2 324 861 A    11/1998
(Continued)

OTHER PUBLICATIONS

Hagelstein et al., "The Energy Calibration of X-Ray Absorption Spectra Using Multiple-Beam Diffraction", Review of Scientific Instruments, vol. 63, No. 1, pp. 911-913 (Jan. 1992).
(Continued)

*Primary Examiner* — Anastasia Midkiff
(74) *Attorney, Agent, or Firm* — Jeffrey Klembczyk, Esq.; Kevin P. Radigan, Esq.; Heslin Rothenberg Farley & Mesiti P.C.

(57) ABSTRACT

An x-ray system or method for exciting a sample under x-ray analysis, using a curved monochromating optic for directing a monochromatic x-ray beam from an x-ray source towards a first focal area. A second optic is positioned within, and receives, the monochromatic x-ray beam, and directs a focused x-ray beam towards a second focal area on the sample. A detector is positioned near the sample to collect radiation from the sample as a result of the focused x-ray beam. The curved monochromating optic produces a beam spot size at the first focal area larger than a beam spot size produced by the second optic at the second focal area, therefore, a beam spot size on the sample is thereby reduced using the second optic. Doubly-curved monochromating optics, and polycapillary optics, are disclosed as possible implementations of the optics.

11 Claims, 6 Drawing Sheets

U.S. PATENT DOCUMENTS

| | | | |
|---|---|---|---|
| 4,599,741 A | 7/1986 | Wittry | |
| 5,175,755 A * | 12/1992 | Kumakhov | 378/34 |
| 5,192,869 A | 3/1993 | Kumakhov | |
| 5,497,008 A | 3/1996 | Kumakhov | |
| 5,812,631 A * | 9/1998 | Yan et al. | 378/85 |
| 5,892,809 A * | 4/1999 | Wittry | 378/85 |
| 6,317,483 B1 * | 11/2001 | Chen | 378/84 |
| 6,345,086 B1 | 2/2002 | Ferrandino et al. | |
| 6,389,107 B1 | 5/2002 | Kantsyrev et al. | |
| 6,504,901 B1 | 1/2003 | Loxley et al. | |
| 6,678,348 B1 * | 1/2004 | Kumakhov | 378/84 |
| 6,697,454 B1 | 2/2004 | Nicolich et al. | |
| 6,934,359 B2 * | 8/2005 | Chen et al. | 378/84 |
| 6,963,072 B2 * | 11/2005 | Kumakhov | 250/505.1 |
| 7,110,503 B1 * | 9/2006 | Kumakhov | 378/119 |
| 2002/0021782 A1 * | 2/2002 | McDonald | 378/84 |
| 2002/0027972 A1 * | 3/2002 | Joy et al. | 378/85 |
| 2002/0159562 A1 * | 10/2002 | Holz | 378/85 |

FOREIGN PATENT DOCUMENTS

JP    2004-333131 A    11/2004

OTHER PUBLICATIONS

Shu et al., "VUV-SX Spherical Grating Monochromator for BEPC Beamline 4B9B", Review of Scientific Instruments, vol. 60, No. 7, part 2B, pp. 2085-2088 (Jul. 1989).

* cited by examiner

MONOCHROMATIC X-RAY MICRO BEAM FOR TRACE ELEMENT MAPPING

CROSS-REFERENCE TO RELATED APPLICATION

This application is a National Stage (371) entry of PCT Application PCT/US2006/028890, filed Jul. 26, 2006, and published under the PCT Articles in English as WO 2007/019053 A1 on Feb. 15, 2007. PCT/US2006/028890 claimed the benefit of U.S. Provisional Application No. 60/705,376, filed Aug. 4, 2005. The present application claims the benefit of U.S. Provisional Application Ser. No. 60/705,376, filed Aug. 4, 2005, which is hereby incorporated herein by reference. This application also contains subject matter which is related to the subject matter of the following applications, each of which is hereby incorporated herein by reference in its entirety:

"AN OPTICAL DEVICE FOR DIRECTING X-RAYS HAVING A PLURALITY OF OPTICAL CRYSTALS," by Zewu Chen, U.S. Ser. No. 11/048,146, filed Feb. 1, 2005, which application is a continuation of PCT Application PCT/US2003/023412, filed Jul. 25, 2003, and published under the PCT Articles in English as WO 2004/013867 A2 on Feb. 12, 2004, which PCT application claimed priority to U.S. Provisional Application No. 60/400,809, filed Aug. 2, 2002.

TECHNICAL FIELD

This invention relates in general to x-ray optics. More particularly, the present invention relates to an arrangement of x-ray optics and an associated system for producing a monochromatic x-ray beam of a highly controlled, small spot size, on a sample for x-ray analysis, including for example x-ray fluorescence and x-ray diffraction analysis.

BACKGROUND OF THE INVENTION

As discussed in certain commonly-assigned, co-pending, published U.S. patent applications related to wavelength dispersive x-ray fluorescence (XRF) systems, the use of monochromating optics in the excitation and/or detection paths provides various advantages, including the ability to narrow the spectrum of wavelengths present at the sample under analysis, thereby increasing the signal-to-background ratio of the system and improving analysis results (e.g., see U.S. application No. 60/336,584 filed Dec. 4, 2001, and entitled "X-Ray Tube and Method and Apparatus for Analyzing Fluid Streams Using X-Rays," perfected as PCT Application PCT/US02/38792-WO03/048745, entitled "X-Ray Tube and Method and Apparatus for Analyzing Fluid Streams Using X-Rays;" and U.S. application No. 60/299,371 filed Jun. 19, 2001, and entitled "XRF System Including Focusing Optic on Excitation Side and Monochromatic Collection," perfected as PCT Application PCT/US02/19272-WO02/103710, entitled "Wavelength Dispersive XRF System Using Focusing Optic for Excitation and a Focusing Monochromator for Collection" all of which are incorporated by reference herein in their entirety).

Similar benefits of such monochromatization can also be applicable to other types of x-ray analysis systems, including, for example, x-ray diffraction systems depending on the particular application. Though not directly addressing monochromatization, advanced diffraction systems are addressed in, for example, commonly assigned U.S. application No. 60/492,400 filed Aug. 4, 2003 entitled "In-Situ X-Ray Diffraction System Using Sources and Detectors at Fixed Angular Positions," perfected as PCT Application PCT/US04/25112-WO2005031329 of the same title; and application No. 60/489,047 filed Jul. 22, 2003 entitled "Method and System for X-Ray Diffraction Measurements Using an Aligned Source and Detector Rotating Around a Sample Surface," perfected as U.S. application Ser. No. 10/893,511 filed Jul. 16, 2004, all of which are incorporated by reference herein in their entirety.

In addition to monochromatic beams, small, intense x-ray beam spot sizes at the sample are also of significant interest in certain x-ray analysis systems. Small spot sizes are usually correlated with increased x-ray intensity as a function of the input x-ray source power and the optic focusing capabilities. Increased power on the sample leads to improved analysis results. However, certain applications require small spot sizes for reasons other than intensity—smaller spot sizes enable higher spatial resolution and therefore more precise elemental mapping of the sample; as well as the ability to isolate certain features on a sample while preventing interfering fluorescence/diffraction returns from other adjacent features on the sample. Excitation beam spot sizes, though dramatically improved in the last few years, are still larger than many integrated circuit (IC) feature sizes now in use (e.g., scribe lines), and those planned for the "nanosystems" of the future.

Small spot sizes also enable small sample aperture sizes in, e.g., high-pressure on-line analysis systems, as discussed at length in the above-incorporated U.S. patent applications.

The monochromating optics discussed in the above-incorporated U.S. patent applications (e.g., doubly curved crystals) can achieve small spot sizes, but usually at the expense of aperture size, and (as fundamentally a device which is imaging the source) as a function of the x-ray source spot size, which may be too large. What is required, therefore, are techniques, methods and systems which exploit the benefits of x-ray monochromatization in e.g., XRF systems, while also providing small, intense, x-ray beam spot sizes.

SUMMARY OF THE INVENTION

The shortcomings of the prior art are overcome and additional advantages are provided through the present invention which in one aspect is an x-ray system or method for exciting a sample under x-ray analysis, using a curved monochromating optic for directing a monochromatic x-ray beam from an x-ray source towards a first focal point. A second optic is positioned within, and receives, the monochromatic x-ray beam, and directs a focused x-ray beam towards a second focal point on the sample. A detector is positioned near the sample to collect radiation from the sample as a result of the focused x-ray beam.

The curved monochromating optic may have an optical surface, the optical surface being doubly-curved, e.g., a doubly curved crystal optic or a doubly curved multilayer optic. The second optic may be a polycapillary optic, or a monocapillary optic.

The curved monochromating optic produces a beam spot size at the first focal point larger than a beam spot size produced by the second optic at the second focal point, therefore, a beam spot size on the sample is thereby reduced using the second optic.

The second optic may be positioned within the monochromatic x-ray beam, before the first focal point, thereby receiving the monochromatic x-ray beam as it converges toward the first focal point. In this case, the second optic is a convergent-beam-to-point focusing optic.

The second optic may also be positioned within the monochromatic x-ray beam, after the first focal point, thereby receiving the monochromatic x-ray beam as it diverges from the first focal point. In this case, the second optic is a divergent-beam-to-point focusing polycapillary optic.

The x-ray source may be an inexpensive, electron-bombardment-type x-ray tube, having a low power of less than 100 watts.

A controller may be provided for monitoring and/or controlling the position of the sample, second focal point, and/or the detector to provide an accurate indication of the location of the focal point on the sample.

The disclosed embodiments of the present invention offer the advantages of monochromatization in the excitation path (which increases the signal-to-background of the system) as well as smaller spot sizes than those otherwise attainable (which provide better spatial resolution, the ability to distinguish between different types of sample features, and/or smaller sample apertures where needed).

BRIEF DESCRIPTION OF THE DRAWINGS

The subject matter regarded as the invention is particularly pointed out and distinctly claimed in the claims at the conclusion of the specification. The foregoing and other objects, features, and advantages of the invention are apparent from the following detailed description taken in connection with the accompanying drawings in which:

DETAILED DESCRIPTION OF THE INVENTION

Figure 1:
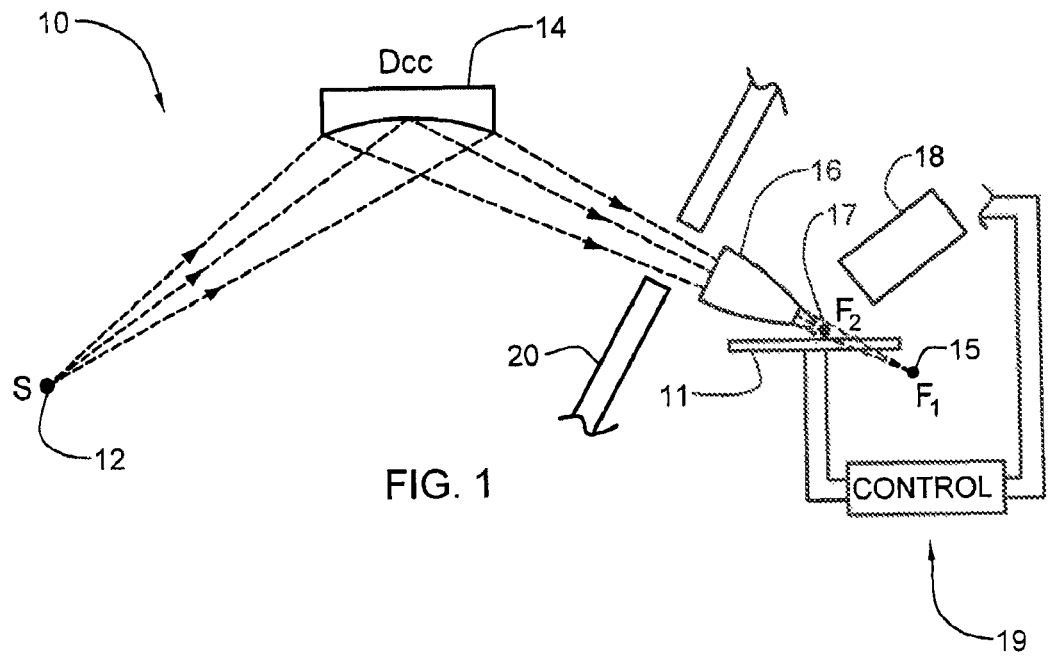
FIG. 1 depicts a first embodiment of the present invention in which an x-ray analysis system includes a first, monochromating optic followed by a second focusing optic positioned prior to its focal point.

In x-ray analysis systems, high x-ray beam intensity, and small beam spot sizes, are important to reduce sample exposure times, increase spatial resolution, and consequently, improve the signal-to-background ratio and overall quality of x-ray analysis measurements. In the past, expensive and powerful x-ray sources, such as rotating anode x-ray tubes or synchrotrons, were the only options available to produce high-intensity x-ray beams. Recently, the development of x-ray optic devices has made it possible to collect the diverging radiation from an x-ray source by focusing the x-rays. A combination of x-ray focusing optics and small, low-power x-ray sources can produce x-ray beams with intensities comparable to those achieved with more expensive devices. As a result, systems based on a combination of small, inexpensive x-ray sources, excitation optics, and collection optics have greatly expanded the availability and capabilities of x-ray analysis equipment in, for example, small laboratories or at line or online production or processing applications.

Monochromatization of x-ray beams in the excitation and/or detection paths is also useful, as discussed above. One existing x-ray monochromatization technology is based on diffraction of x-rays on optical crystals, for example, germanium (Ge) or silicon (Si) crystals. Curved crystals can provide deflection of diverging radiation from an x-ray source onto a target, as well as providing monochromatization of photons reaching the target. Two common types of curved crystals are known as singly-curved crystals and doubly-curved crystals (DCC). Using what is known in the art as Rowland circle geometry, singly-curved crystals provide focusing in two dimensions, leaving x-ray radiation unfocused in the third or orthogonal plane. Doubly-curved crystals provide focusing of x-rays from the source to a point target in all three dimensions. This three-dimensional focusing is referred to in the art as "point-to-point" focusing.

The point-to-point focusing property of doubly-curved crystals has many important applications in, for example, material science structural analysis. Depending on the bending radii of the doubly-curved crystal in the Rowland optic circle plane, curved crystals further divide into Johansson and Johann types. Typically, Johansson geometry requires crystals to have a curvature that is equal to the radius of the Rowland circle, while Johann geometry configuration may have a curvature twice the radius of the Rowland circle.

The present invention, in one embodiment, is directed to an x-ray analysis system using monochromatic excitation to improve signal-to-background ratio significantly, compared to the use of polychromatic excitation. As discussed above, doubly-curved crystal (DCC) optics can provide high intensity monochromatic focused beam using a low power x-ray tube. However, since the focal spot of a DCC optic is strongly dependent on the x-ray tube spot size and also the optic aperture, it can be difficult to achieve a beam spot of less than the spot size of the source (in one source example, 70 μm).

The present invention is directed to a novel x-ray optic which enables small spot, monochromatic beams for mapping of elements, with a high spatial resolution. For example, a spot size of less than 17 μm can be achieved (compared to an imaged source having a 70 μm spot). A spot size of about 1 micrometer can be achieved with a monocapillary optic. Two beam energies, Mo Kα and Cu Kα, have been considered for this approach.

With reference to FIG. 1, x-ray analysis system 10 includes a source 12, and a curved, monochromating optic 14. In general (though not required), optic 14 images an x-ray beam produced by source 12 towards an output focal point 15 (F1). A second, focusing optic 16 is placed in this beam path (which is converging on point 15), and receives the beam prior to its focal point 15 at the optic's input end. The second optic is designed, e.g., as a convergent-beam-to-point optic, and provides a second level of focusing to its own output focal point 17 (F2) on a sample 11 under analysis. (Note, focal point 15 is discussed only as a basis to describe the operation of optic 14. Since the beam is re-directed prior to this point, x-rays may not actually "exist" at that point.) Convergent-beam-to-point optics can be implemented using polycapillary optics such as those disclosed in commonly assigned, X-Ray Optical Systems, Inc. U.S. Pat. Nos. 5,192,869; 5,175,755; 5,497,008; 5,745,547; 5,570,408; and 5,604,353; the entirety of which are incorporated herein by reference herein in their entirety. In addition to the "barrel" and "half-barrel" optics disclosed in those patents, polycapillary optics such as a conical optic, with non-bent but contracting capillary diameters can also be used. Monocapillary optics can also be used, such as those disclosed in commonly assigned, X-Ray Optical Systems, Inc. U.S. Pat. No. 5,747,821; the entirety of which is incorporated herein by reference herein in its entirety. In general, such optics should be capable of re-focusing x-ray energy, and be of the reflecting (rather than absorbing) type.

Such focusing optics can capture x-ray beams and focus to small beam spot sizes on the order of 17 μm or less, depending on the input energy level. This beam spot size is smaller than that attainable using the source 12/optic 14 configuration alone, especially considering, as discussed above, that optic 14 may be limited to imaging the spot size of the source 12, which in one example is about 70 μm (using an x-ray tube available from Oxford Instruments—#5011). In the disclosed configuration, the source 12/optic 14 combination provides a "virtual source" for focusing optic 16, which in turn provides the additional level of focusing.

Figure 2:
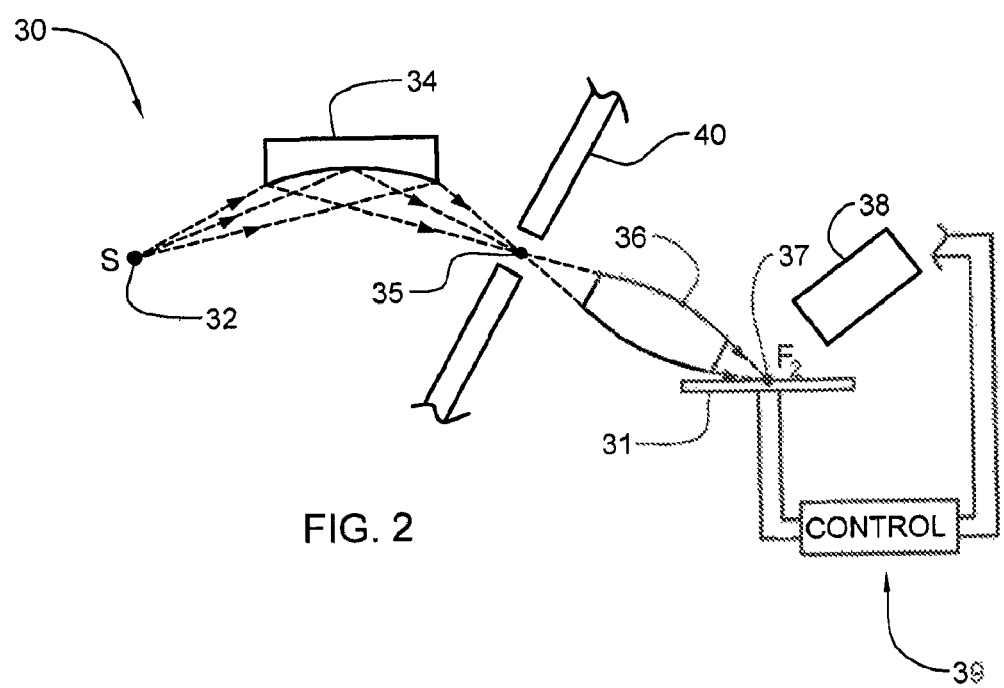
FIG. 2 depicts a second embodiment of the present invention in which an x-ray analysis system includes a first, monochromating optic followed by a second focusing optic positioned beyond its focal point.

In an alternate embodiment of the present invention, with reference to FIG. 2, x-ray analysis system 30 includes a source 32, and a curved, monochromating optic 34. In general (though not required), optic 34 images an x-ray beam produced by source 32 towards an output focal point 35 (F1). As shown, and consistent with the operation of point imaging optics, this beam may first converge towards its focal point 35, and then diverges beyond this focal point. In this embodiment, a second, focusing optic 36 is placed in this beam path (which is diverging beyond focal point 35), and receives this beam beyond its focal point at the optic's input end. The second optic is designed as a divergent-beam-to-point optic, and provides a second level of focusing to its own output focal point 37 (F2) on a sample under analysis 31. Divergent-beam-to-point optics can be implemented using polycapillary optics such as those disclosed in the above-incorporated U.S. Pat. Nos. 5,192,869; 5,175,755; 5,497,008; 5,745,547; 5,570,408; and 5,604,353; polycapillary conical optics; and monocapillary optics as discussed above. Again, such optics should be capable of re-focusing x-ray energy, and be of the reflecting (rather than absorbing) type. As in the first embodiment, such optics can capture x-ray beams and focus to small beam spot sizes on the order of 17 μm or less, depending on the input energy level. This beam spot size is smaller than that attainable using the source 32/optic 34 configuration alone, especially considering, as discussed above, that optic 34 may be limited to imaging the spot size of the source 32, which in one example is about 70 μm (using an x-ray tube available from Oxford Instruments—#5011). In this configuration, the source 32/optic 34 combination provides a "virtual source" for focusing optic 36, which in turn provides an additional level of focusing.

Also shown in FIGS. 1 and 2 are portions of a shielding or cabinet 20, 40, respectively. This shielding or cabinet can include a relatively small aperture for passing the x-ray beam from DCC 14, 34, respectively, at a point on the beam where it has been significantly narrowed by the optic 14, 34. This shielding can be advantageously used to isolate the detection subsystem from x-ray background noise generated by the source and first optic. Eliminating this background noise can dramatically improve measurement results.

Though point focusing is disclosed in these embodiments, those skilled in the art will recognize that the present invention can extend to fine-line focusing as well, in which case the monochromating optic focuses to a first focal line (or rectangle), and a polycapillary optic (e.g., in a generally rectangular shape) re-focuses the line to a finer line. Or, in another embodiment, the monochromating may produce a parallel beam, of, for example, substantially uniform cross-sectional shape along its beam path. The second, focusing optic can be a parallel-to-point focusing optic placed anywhere along this path (and in fact translatable along this path) to provide a variable output focal spot position. This can assist in elemental mapping of a sample, using a small, but moveable beam spot on the sample, using only the movement of the second optic. Also, in either of the embodiments of FIGS. 1 and 2 above (especially for diffraction) the second optic could be either a convergent-beam-to parallel optic, or (preferred) divergent-beam-to-parallel optic; otherwise known as a collimating optic. These types of collimating optics are also disclosed in the above-incorporated U.S. patent applications. In all of these cases, it is important to note that both optics of the present invention are changing the convergence/divergence path of the beam in some appreciable way. This beam convergence/divergence shaping is distinguished from other flat crystal optics, or slit optics. Therefore, for the purposes of this application, the terms "focus," "focusing" or "focused" connote some appreciable change of the convergence or divergence of the input beam, toward a focal "area" (e.g., line, point, rectangle, etc.) Point focusing optics are shown in FIGS. 1 and 2 for illustration only and those skilled in the art will recognize that the focal "areas" of the optics can be customized to any particular shape.

In both embodiments, detectors 18 and 38 respectively are arranged over/about the sample to collect the resultant x-ray radiation from the sample (e.g., diffraction, fluorescence, etc.) as discussed in the above-incorporated U.S. patents and patent applications, and provide the requisite analytical results through systems 19/39. In fact, in certain applications detection path optics can be used for additional monochromatization (in, for example, the above-incorporated XRF patent applications which discuss wavelength dispersive spectrometry and the relevant detectors) and angular filtering (in, for example, the above-incorporated XRD patent applications which discuss a variety of applicable detection schemes).

All of the components, including sample positioning stages (not shown), can be controlled and/or monitored by a controller 19/39, which can collect positional data from any of the elements/beams shown, and provide trace element mapping across the sample according to the resolution offered by the small x-ray beam spot size of the present invention, i.e., 17 μm or less. This is a fundamental advantage of the present invention—the ability to perform trace element mapping over a sample surface with a high degree of accuracy driven by the small beam spot size. CCD cameras can be used within these systems to obtain the positional data required.

Figure 3:
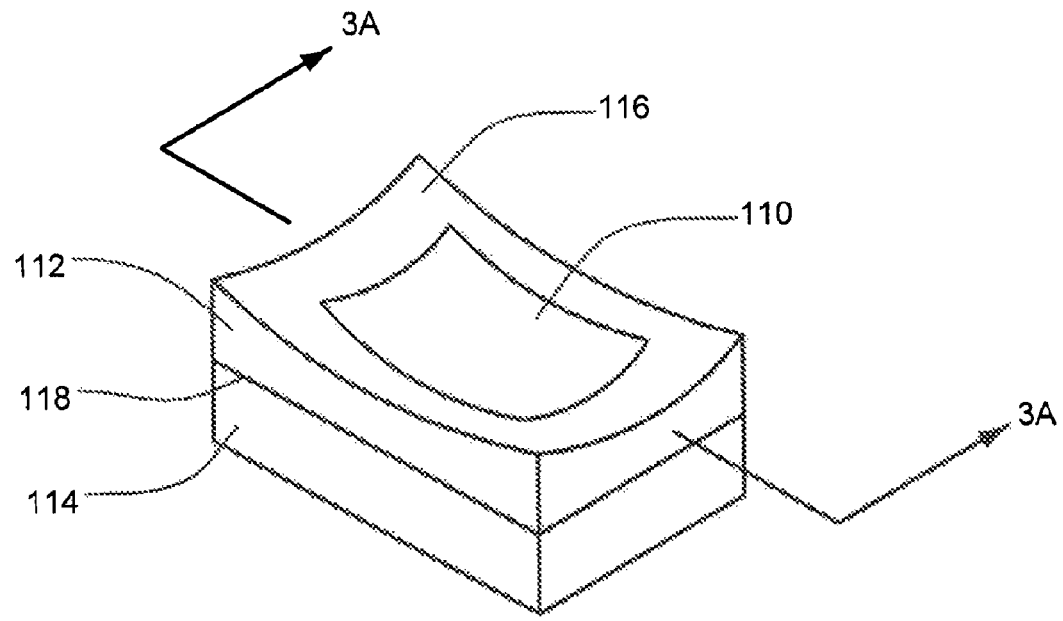
FIG. 3 depicts one embodiment of a point-focusing, doubly curved monochromating optic.
Figure 3A:
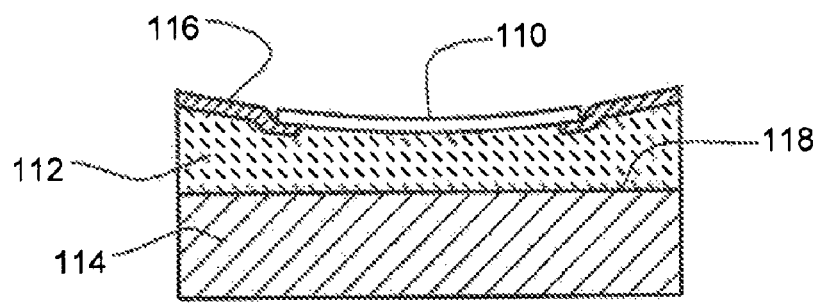
FIG. 3A is a cross-sectional, elevational view of the optic of FIG. 3, taken along line A-A.

Example DCC Optic Technology:

The curved, monochromating optics 14 and 34 can comprise various optical devices, including a doubly-curved crystal (DCC) optic or a doubly-curved multilayer optic. One embodiment of such a doubly-curved optical device is depicted in FIGS. 3 and 3A, and is described in detail in U.S. Pat. No. 6,285,506 B1, issued Sep. 4, 2001, the entirety of which is hereby incorporated herein by reference.

In the embodiment of FIG. 3, a doubly-curved optical device includes a flexible layer 110, a thick epoxy layer 112 and a backing plate 114. The structure of the device is shown further in the cross-sectional elevational view in FIG. 3A.

In this device, the epoxy layer 112 holds and constrains the flexible layer 110 to a selected geometry having a curvature. Preferably, the thickness of the epoxy layer is greater than 20 μm and the thickness of the flexible layer is greater than 5 μm. Further, the thickness of the epoxy layer is typically thicker than the thickness of the flexible layer. The flexible layer can be one of a large variety of materials, including: mica, Si, Ge, quartz, plastic, glass etc. The epoxy layer 112 can be a paste type with viscosity in the order of $10^3$ to $10^4$ poise and 30 to 60 minutes pot life. The backing plate 114 can be a solid object that bonds well with the epoxy. The surface 118 of the backing plate can be flat (FIG. 3A) or curved, and its exact shape and surface finish are not critical to the shape and surface finish of the flexible layer. In the device of FIGS. 3 & 3A, a specially prepared backing plate is not required.

Surrounding the flexible layer may be a thin sheet of protection material 116, such as a thin plastic, which is used around the flexible layer edge (see FIG. 3A). The protection material protects the fabrication mold so that the mold is reusable, and would not be necessary for a mold that is the exact size or smaller than the flexible layer, or for a sacrificial mold.

Figure 4:
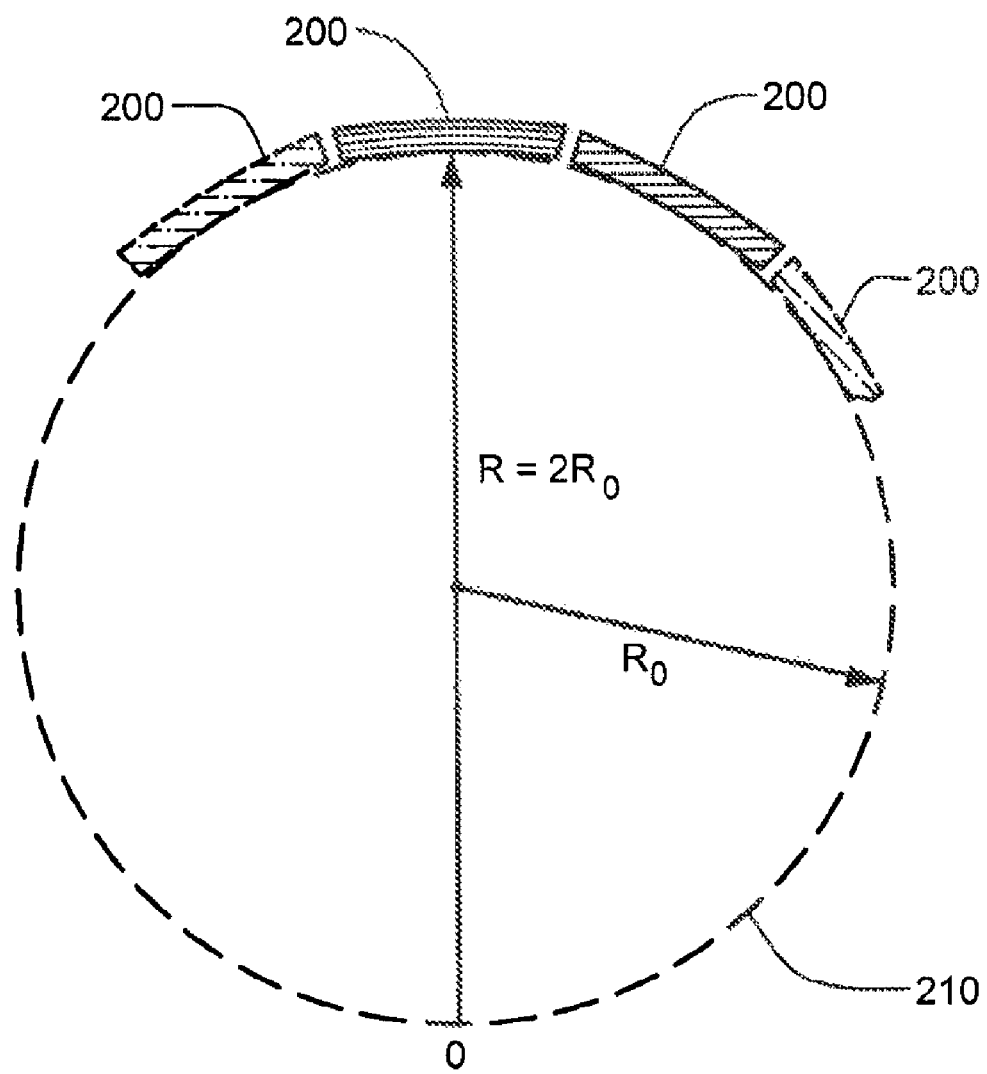
FIG. 4 depicts another possible embodiment of a focusing, curved monochromating optic (and illustrating Rowland circle geometry)

Doubly-curved optical devices, such as doubly-curved crystal (DCC) optics, are now used in material analysis to collect and focus x-rays from a large solid angle and increase the usable flux from an x-ray source. Three-dimensional focusing of characteristic x-rays can be achieved by diffraction from a toroidal crystal used with a small x-ray source. This point-to-point Johan geometry is illustrated in FIG. 4. The diffracting planes of each crystal optic element 200 can be parallel to the crystal surface. If the focal circle 210 containing a point source and the focal point has radius $R_0$, then the crystal surface has, for example, a radius R of curvature of $2R_0$ in the plane of the focal circle and a radius of curvature of $r=2R_0 \sin^2\theta_{Brag}$ in the perpendicular plane, with the radius centered on a line segment drawn between the source and the focal point. X-rays diverging from the source, and incident on the crystal surface at angles within the rocking curve of the crystal will be reflected efficiently to the focal or image point. The monochromatic flux density at the focal point for a DCC-based system is several orders of magnitude greater than that of conventional systems with higher power sources and similar source to object distances. This increase yields a very high sensitivity for use in many different applications, including (as described herein) x-ray fluorescence and diffraction.

As a further enhancement, FIG. 4 illustrates that the optical device may comprise multiple doubly-curved crystal optic elements 200 arranged in a grid pattern about the Rowland circle. Such a structure may be arranged to optimize the capture and redirection of divergent radiation via Bragg diffraction. In one aspect, a plurality of optic crystals having varying atomic diffraction plane orientations can be used to capture and focus divergent x-rays towards a focal point. In another aspect, a two or three dimensional matrix of crystals can be positioned relative to an x-ray source to capture and focus divergent x-rays in three dimensions. Further details of such a structure are presented in the above-incorporated, co-pending U.S. patent application Ser. No. 11/048,146, entitled "An Optical Device for Directing X-Rays Having a Plurality of Optical Crystals".

Figure 5:
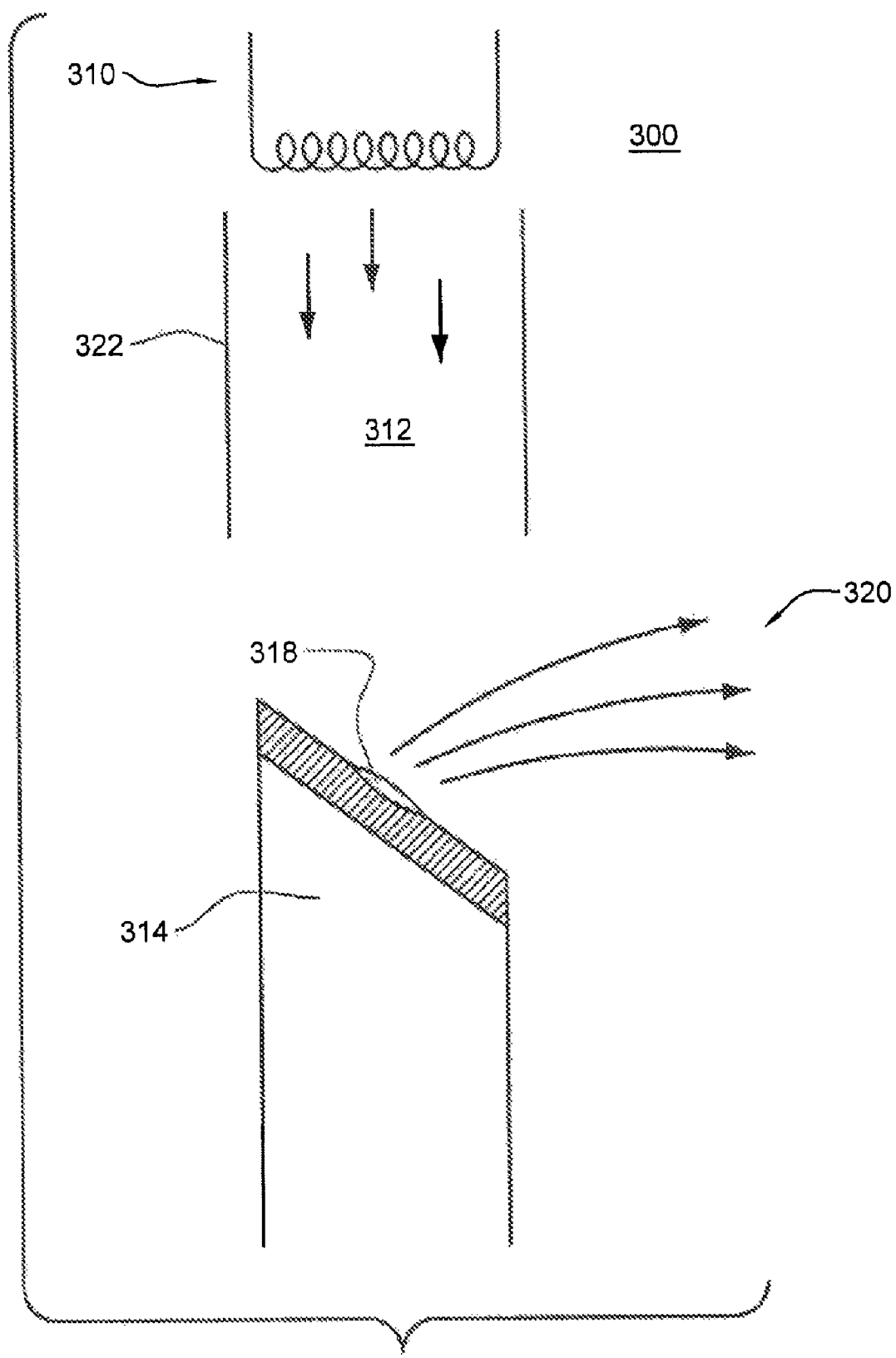
FIG. 5 depicts a small, inexpensive electron bombardment x-ray source useable in the present invention.

Example Source/Optic Technology:

As discussed above, the ability to provide an efficient and economical analysis capability depends to a large extent upon source/optic technology. In that regard, certain source and optic technology can be combined for such systems, as discussed below with respect to FIG. 5 in which the basic elements of a typical compact, electron-bombardment x-ray source 300 are shown. Electron gun/filament 310 is heated (by applying a voltage) to a temperature such that electrons 312 are thermally emitted. These emitted electrons are accelerated by an electric potential difference to anode 314, which is covered with target material, where they strike within a given surface area of the anode, called the spot 318. Divergent x-rays 320 are emitted from the anode as a result of the collision between the accelerated electrons and the atoms of the target. One example of this type of x-ray tube is available from Oxford Instruments—model #5011, which operates at less than 100 watts (i.e., 75 watts) at a cost of less than $1500 per tube, in contrast to higher-power, laboratory sources which can cost many thousands, or hundreds of thousands of dollars—which is cost prohibitive for many applications.

Source/optic combinations are also useable for the source 12, 32/optic 14, 34 combinations above, such as those disclosed in X-Ray Optical Systems, Inc.'s U.S. Pat. No. 5,570,408, issued Oct. 29, 1996, as well as in U.S. Provisional Application Ser. Nos. (1) 60/398,968 (filed Jul. 26, 2002, entitled "Method and Device for Cooling and Electrically-Insulating a High-Voltage, Heat-Generating Component," and perfected as PCT Application PCT/US02/38803); (2) 60/398,965 (filed Jul. 26, 2002, entitled "X-Ray Source Assembly Having Enhanced Output Stability," and perfected as PCT Application PCT/US02/38493); (3) 60/492,353 (filed Aug. 4, 2003, entitled "X-Ray Source Assembly Having Enhanced Output Stability Using Tube Power Adjustments and Remote Calibration"); and (4) 60/336,584 (filed Dec. 4, 2001, and entitled "X-Ray Tube and Method and Apparatus for Analyzing Fluid Streams Using X-Rays," perfected as PCT Application PCT/US02/38792-WO03/048745, entitled "X-Ray Tube and Method and Apparatus for Analyzing Fluid Streams Using X-Rays")—all of which are incorporated by reference herein in their entirety.

The disclosed embodiments of the present invention offer the advantages of monochromatization in the excitation path (which increases the signal-to-background of the system) as well as smaller spot sizes than those otherwise attainable (which provide better spatial resolution, the ability to distinguish between different types of sample features, and/or smaller sample apertures where needed).

Figure 6:
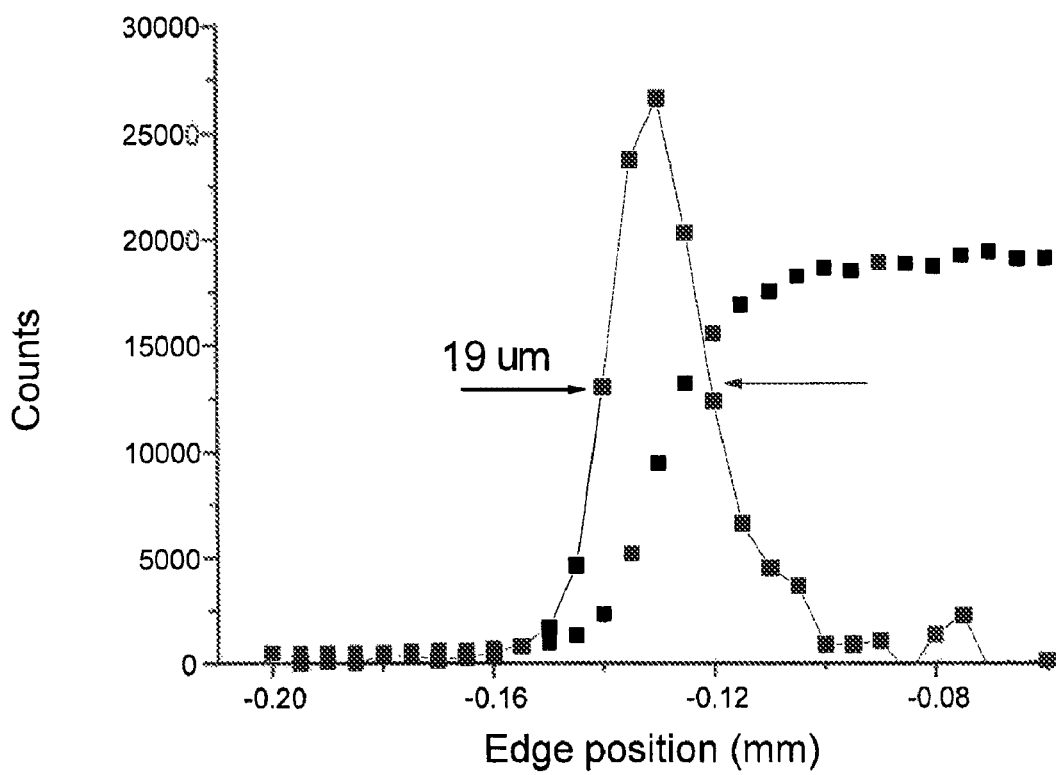
FIGS. 6-8 show results of the present invention, when arranged according to the principles of FIG. 1.
Figure 7:
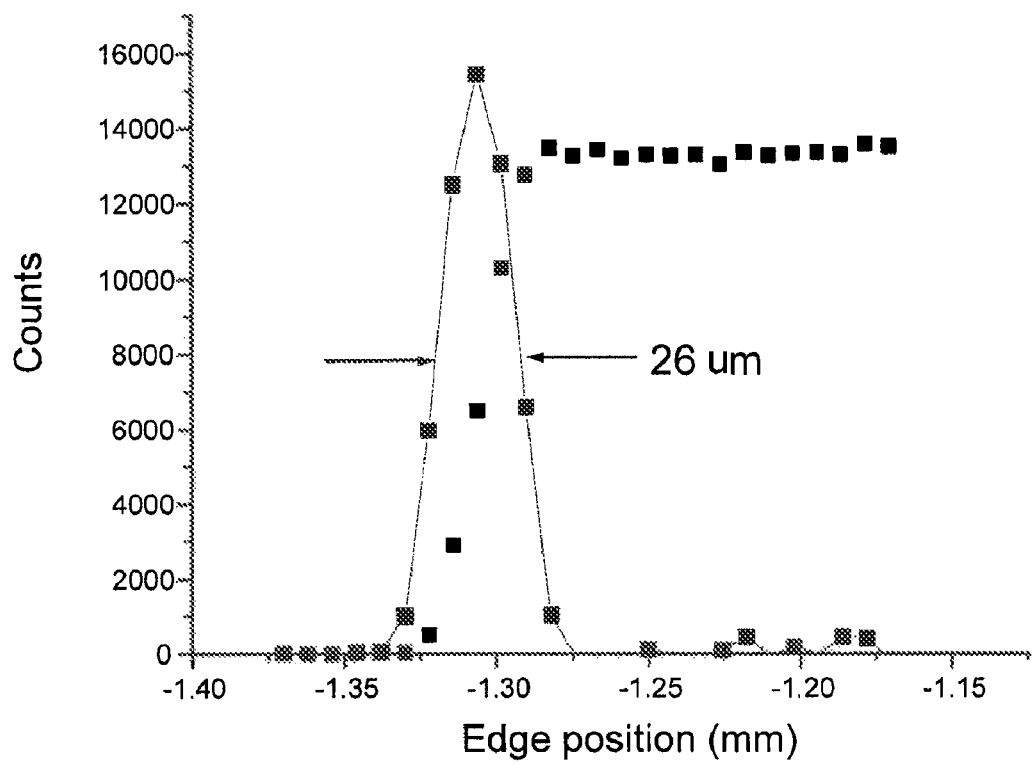
Figure 8:
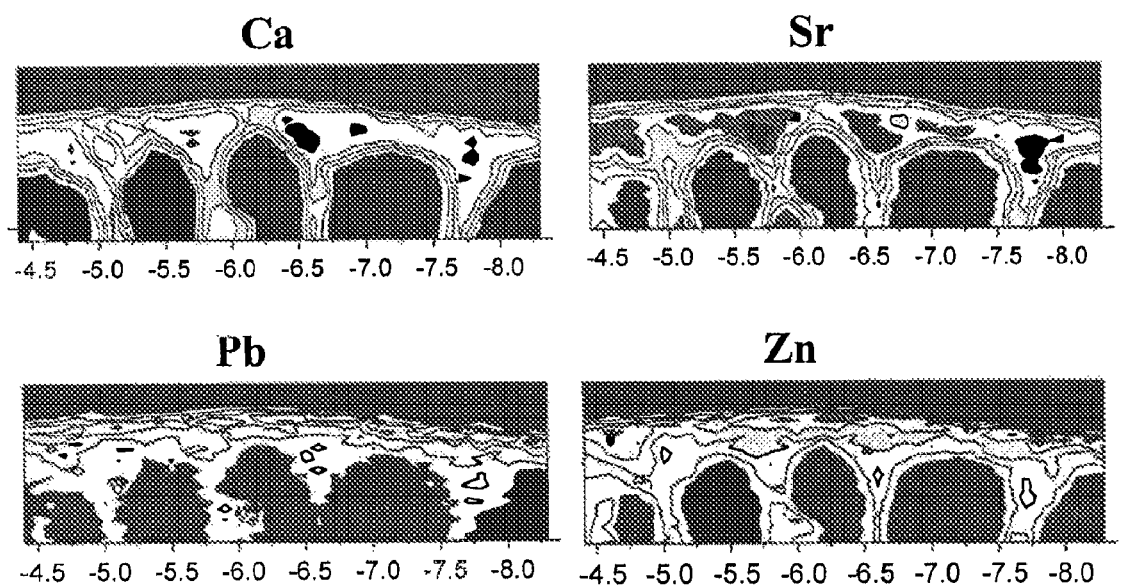

FIGS. 6-8 show results of the present invention, when arranged according to the principles of FIG. 1. FIG. 6 shows a knife-edge scan of the resultant spot size (i.e., 19 μm) using a source with an Mo target and MoKa energy. FIG. 7 shows a knife-edge scan of the resultant spot size (i.e., 26 μm) using a source with a Cu target and CuKa energy. FIG. 8 shows an x-ray fluorescence, trace element mapping of a bone section for 4 different elements—using the small spot size produced by the present invention.

Although preferred embodiments have been depicted and described in detail herein, it will be apparent to those skilled in the relevant art that various modifications, additions, substitutions and the like can be made without departing from the spirit of the invention and these are therefore considered to be within the scope of the invention as defined in the following claims.

What is claimed is:

1. An x-ray system for exciting a sample under x-ray analysis, comprising:

a curved, point-to-point focusing monochromating optic for redirecting and focusing a monochromatic x-ray beam from an x-ray source towards a first focal point;

a second, convergent-beam-to-point focusing optic positioned within, and receiving, the monochromatic x-ray beam, and directing a focused x-ray beam towards a second focal point on the sample; and a detector positioned near the sample to collect radiation from the sample as a result of the focused x-ray beam;

wherein the curved monochromating optic produces a beam spot size at the first focal point larger than a beam spot size produced by the second optic at the second focal point, wherein a beam spot size on the sample is thereby reduced using the second optic;

wherein the second optic is positioned within the monochromatic x-ray beam, before the first focal point, thereby receiving the monochromatic x-ray beam as it converges toward the first focal point.

2. The x-ray system of claim 1, wherein the curved monochromating optic comprises an optical surface, the optical surface being doubly-curved.

3. The x-ray system of claim 2, wherein the monochromating optic is a doubly curved crystal optic.

4. The x-ray system of claim 2, wherein the monochromating optic is a doubly curved multilayer optic.

5. The x-ray system of claim 2, wherein the second optic is a polycapillary optic.

6. The x-ray system of claim 2, wherein the second optic is a monocapillary optic.

7. The x-ray system of claim 1, wherein the at least one curved monochromating optic comprises a plurality of doubly-curved optical crystals or a plurality of doubly-curved multilayer optics.

8. The x-ray system of claim 1, wherein the second focal point on the sample is positioned between the second optic and the first focal point.

9. The x-ray system of claim 1,
wherein the x-ray source comprises an electron-bombardment-type x-ray tube.

10. The x-ray system of claim 9, wherein the x-ray tube is a low power x-ray tube of less than 100 watts.

11. The x-ray system of claim 1, further comprising:
a controller for monitoring and/or controlling the position of the sample, the second focal point, and/or the detector to provide an accurate indication of the location of the second focal point on the sample.

* * * * *